United States Patent [19]

Slack et al.

[11] Patent Number: 5,326,829

[45] Date of Patent: Jul. 5, 1994

[54] PROCESS FOR THE PRODUCTION OF ACTIVATED POLYETHERS

[75] Inventors: William E. Slack, Moundsville; Rick L. Adkins, New Martinsville, both of W. Va.

[73] Assignee: Miles Inc., Pittsburgh, Pa.

[21] Appl. No.: 957,921

[22] Filed: Oct. 7, 1992

[51] Int. Cl.$^5$ .............................................. C08G 65/32
[52] U.S. Cl. .............................. 525/403; 252/182.17; 252/182.26; 564/505; 568/589
[58] Field of Search ............. 252/182.17, 182.26; 568/589; 564/505, 301, 511, 512, 475, 477; 525/403

[56] References Cited

U.S. PATENT DOCUMENTS

| | | | |
|---|---|---|---|
| 3,862,973 | 1/1975 | Dietrich et al. | 260/453 AB |
| 4,618,706 | 10/1986 | Scholl et al. | 560/335 |
| 5,015,774 | 5/1991 | Suekane et al. | 564/475 |
| 5,112,979 | 5/1992 | Lin et al. | 546/244 |
| 5,114,755 | 5/1992 | Canaday et al. | 427/373 |

FOREIGN PATENT DOCUMENTS

| | | | |
|---|---|---|---|
| 363877 | 4/1990 | European Pat. Off. | 564/505 |
| 489322 | 6/1992 | European Pat. Off. | |
| 0161938 | 8/1985 | Japan | 568/589 |

*Primary Examiner*—John Kight, III
*Assistant Examiner*—Rachel Johnson
*Attorney, Agent, or Firm*—Joseph C. Gil; Godfried R. Akorli; Lyndanne M. Whalen

[57] ABSTRACT

Disclosed herein is a method of preparing an activated polyether polyol by reacting an aminoalcohol with a polyether terminated with a leaving group.

3 Claims, No Drawings

PROCESS FOR THE PRODUCTION OF ACTIVATED POLYETHERS

BACKGROUND OF THE INVENTION

1. Field of Invention

The present invention relates to a process for preparing activated polyether polyols having a low viscosity and a good reactivity which are particularly suitable for resin transfer molding systems.

2. Brief Description of the Prior Art

Polyethers polyols and process for preparing and using the same are known in the art. Of particular interest here are internally catalyzed polyether polyols which offer a faster reactivity towards isocyanates than ordinary hydroxyl group-containing materials but slower reactivity than ordinary amine group-containing materials. These activated polyether polyols are useful in resin transfer molding systems. As would be realized, there is an ongoing research into the preparation of polyethers, which have desirably fast reactivity and processability at the same time.

U.S. Pat. No. 3,654,370 discloses amine-terminated polyethers which are prepared by reacting polyols with ammonia under catalyzed high temperature reaction conditions.

U.S. Pat. No. 4,902,768 discloses N-(polyoxyalkyl)-N-(alkyl)amine by catalytic amination of an appropriate polyol by reacting the polyol with a primary or secondary amine in the presence of a catalyst such as nickel.

U.S. Pat. No. 5,015,774 discloses a process for preparing polyoxyalkylene polyamines having secondary amino groups at the end of the polyamine by reacting a polyoxyalkylene polyol with a primary amine in the presence of a catalyst containing nickel and zinc, cobalt and zinc or, zinc and nickel.

By the present invention, there is provided an efficacious method of preparing activated polyethers polyols which by virtue of the activation are very well suited to use in RIM systems.

SUMMARY OF THE INVENTION

In accordance with the foregoing, the present invention relates to a method of preparing an activated polyether polyol by reacting an aminoalcohol such as a N-alkylaminoalcohol, N-arylaminoalcohol or a dialcoholamine with a polyether containing a good terminal leaving group, at a temperature of 50° to 250° C. By the term activated polyether polyol is meant a polyether polyol which contains within its backbone, a tertiary amine group.

A good leaving group is that which can be displaced at the carbon atom by nucleophiles such as nitrogen, oxygen, sulfur, etc. or the anions of these nucleophiles. As would be realized, the rate at which displacement occurs depends on the chemical nature of the leaving group, and the more stable the free entity of the leaving group is, the easier the leaving group is displaced. Hence, a good leaving group is that which is effective in producing reaction products in accordance with the invention, as described herein.

The resultant activated polyether polyols contain tertiary amine groups which are believed, to act as internal catalysts. This and other aspects of the invention are described more fully hereunder.

DETAILED DESCRIPTION OF THE INVENTION

The activated polyethers of this invention have a functionality of between 1 and 6, and a molecular weight of from 106 to 6000. They are further characterized in that they have relatively low viscosities ranging from about 50 to 5000 centipoises, and an equivalent weight based on their hydroxyl functional group ranging from 50 to 2500. As set forth above, the activated polyether is prepared by reacting a polyether containing a terminal leaving group with an aminoalcohol selected from the group consisting of a N-alkylaminoalcohol, N-arylaminoalcohol and a dialcoholamine, at a temperature of about 50 to 250 degrees Centigrade.

The polyether containing a terminal leaving group can be obtained by converting the hydroxyl group of a polyether polyol to a suitable leaving group. Illustrative but non-limiting examples of the leaving groups can be selected from the group consisting of a halide, a sulfonate (mesylate), a nitrophenoxy group and the like.

Illustrative but non-limiting examples of the polyethers containing hydroxyl groups suitable for use in accordance with the invention can be obtained by the polymerization of alkylene oxides such as ethylene oxide, propylene oxide, butylene oxide, tetrahydrofuran, styrene oxide or epichlorohydrin on their own, in the presence of for example boron trifloride, or by the addition of these epoxides, optionally in admixture or successively onto starter components containing reactive hydrogen atoms, such as water, alcohols or amines, for example ethylene glycol, 1,3- or 1,2-propylene glycol, trimethylol propane, 4,4'-dihydroxydiphenyl propane, aniline, ammonia, ethanolamine or ethylene diamine or a mixture thereof.

In preparing a polyether containing a halide leaving group, e.g., a polyether alkyl halide, a halogenation agent corresponding to the halide is reacted with a polyether polyol. Generally, such a reaction can be conducted at a temperature ranging from −30 to 40 degrees Centigrade over a period of up to 8 hours. Illustratively, in preparing a polyether containing a halide leaving group, a polyether polyol is reacted with a halogenation agent such as carbonyl chloride, (alternately referred to herein as phosgene) typically, a temperature ranging from 0 to 40 degrees Centigrade over a period of 2 to 8 hours. The resultant product rearranges at temperatures from 75 to 150 and preferably 100 to 120 degrees Centigrade, in the presence of a tertiary amine or amide to produce polyether alkyl chloride. Other halogenation agents that can be reacted with a polyether polyol can be thionyl chloride, or triphenyl phosphine in carbon tetrachloride.

In preparing a polyether containing a sulfonate leaving group, e.g., a polyether sulfonate, a polyether polyol can be reacted with methanesulfonyl chloride in the presence of a tertiary amine or amide. The reaction can be conducted at a temperature in the range of −30 to 40 degrees Centigrade. Non-limiting examples of the tertiary amine can be pyridine, triethylamine, tributyl amine. Non-limiting example of the amide can be N,N-dimethylformamide or N,N-dibutylformamide.

Aminoalcohols selected from the group consisting of N-alkylaminoalcohols, N-arylaminoalcohols and dialcoholamines are reacted with the polyether containing a leaving group over a temperature range of 50 to 250 degrees Centigrade to produce the activated polyethers of the invention. The useful N-alkylaminoalcohols N- arylaminoalcohols and dialcoholamines can contain from 1 to 18 and preferably 3 to 12 carbon atoms. Non-limiting examples of aminoalcohols can be selected from the group consisting of N-methylaminoethanol, N-ethylaminoethanol diethanolamine, diisopropanolamine, N-phenylethanolamine 2-(tertbutylamino)ethanol, N-butyl-ethanolamine, N-propyl-ethanolamine.

The ratio of mole(s) of aminoalcohol to equivalents of leaving group of the polyether is of between 12 to 1 and 1 to 1 and preferably 3 to 1. It is believed that the leaving group of the polyether undergoes a displacement reaction to form the activated polyether.

Sodium bicarbonate, sodium hydroxide, or tertiary amines can be employed as acid scavengers in the displacement reaction. Any good solvent such as methylene chloride, toluene, chlorobenzene, or tetrahydrofuran (THF) can be used in the above reactions, if desired.

The resultant activated polyethers are obtained in high conversions (greater that 90%) with relatively low viscosities of from 50 centipoises for 100 equivalent weight difunctional activated polyether to 2000 centipoises for a 2000 equivalent weight trifunctional activated polyether.

This and other aspects of the invention are further described by the following non-limiting examples.

EXAMPLES

In the Examples which follow, the polyether polyol used was a glycerine/propylene oxide/ethylene oxide adduct, with the ethylene oxide being present as a 17% by weight termination, having a 4800 molecular weight.

Chloroformate Preparation

Polyol A (3.0 eq) was added to a 5 L 3-necked flask fitted with a stirrer and dry ice/acetone condenser. Phosgene (3.75 moles) was added at 1.5 mol/h, keeping the reaction temperature below 35° C. After the phosgene addition was complete, the reaction mixture was stirred at room temperature for an additional 2 hours. The chloroformate was purged with $N_2$ at 40° C. to remove residual phosgene. Titration of Chloroformate A showed 100% conversion.

Mesylate Preparation

Polyol A (0.312 eq), triethylamine (0.350 mol), and 60 mL $CH_2Cl_2$ were added to a 2 L 3-necked flask fitted with a stirrer and reflux condenser (under nitrogen). Methane sulfonyl chloride (0.350 mol) was added dropwise, keeping the solution temperature at 25° C. with an ice water bath. The reaction solution was stirred at room temperature for 0.5 h, then neutralized with NaOH (0.350 mol). Triethylamine, solvent, and water were vacuum stripped and the product filtered to give a clear, colorless liquid. (Mesylate A)

EXAMPLE 1

Chloroformate A (0.18 eq) was added to a 12 L 3-necked flask fitted with a stirrer and reflux condenser. The flask was purged with nitrogen and the chloroformate was heated to 60° C. N,N-Dimethylformamide (0.36 mol) was added, keeping the reaction temperature at 60° C. The reaction solution was then heated at 100° C. for 1 h, after which the DMF was vacuum stripped. 2(Methylamino)ethanol (1.08 mol) was added and the solution was heated at 150° C. for 1.5 h. The solution was cooled and neutralized with NaOH (0.18 mol). Excess 2(methylamino)-ethanol was vacuum stripped and the product filtered to give a clear, light yellow liquid with a viscosity of 890 mPa.s and an amine of 26.7. The conversion was 80% based on the amine number.

EXAMPLE 2

Mesylate A (0.060 eq) was added to a 500 mL 3-necked flask fitted with a stirrer and reflux condenser (under nitrogen). 2-(Methylamino)ethanol (0.18 mol) was added and the solution was heated at 150° C. for 2 h. The solution was cooled and neutralized with NaOH (0.060 mol). Excess amine and water were vacuum stripped and the product filtered to give a clear, light yellow liquid with a viscosity of 860 mPa.s and an amine # of 33.2. The conversion was 98% based on the amine number.

EXAMPLES 3-5

These Examples were run using conditions identical with Example 2, keeping moles/equivalents ratios constant. (See Table I)

TABLE 1

| | | Activated Polyol Formation Via Displacement | | | | |
|---|---|---|---|---|---|---|
| Example | Mesylate | Amine | Temp | Time hr. | Amine (NH)# | % Conversion (based on NH#) | Viscosity mPa · s, 25° C. |
| 3 | A | 2-(tert-Butylamino)-ethanol | 150 | 2.0 | 28.7 | 87.1 | 1660 |
| 4 | A | Diethanolamine | 150 | 2.0 | 30.1 | 90.7 | 1740 |
| 5 | A | Diisopropanolamine | 100 | 2.0 | 31.1 | 95.2 | 1600 |

What is claimed is:

1. A method of preparing an activated polyether polyol by reacting an aminoalcohol selected from the group consisting of N-alkylaminoalcohol, N-arylaminoalcohol and dialcoholamine having 1 to 18 carbon atoms in the alkyl or aryl moiety with a polyether terminated by a good leaving group selected from the group consisting of a halide, a sulfonate and a nitrophenoxy group, at 50° to 250° C. which polyether polyol is activated by a resulting tertiary amine group.

2. The method of claim 1 wherein the aminoalcohol contains from 1 to 6 hydroxyl groups.

3. The method of claim 1 wherein the leaving groups is a halide or a sulfonate.

* * * * *